US006969402B2

(12) United States Patent
Bales et al.

(10) Patent No.: US 6,969,402 B2
(45) Date of Patent: Nov. 29, 2005

(54) HELICAL STENT HAVING FLEXIBLE TRANSITION ZONE

(75) Inventors: Thomas O. Bales, Coral Gables, FL (US); Kenneth E. Perry, Bainbridge Island, WA (US)

(73) Assignee: Syntheon, LLC, Miami, FL (US)

( * ) Notice: Subject to any disclaimer, the term of this patent is extended or adjusted under 35 U.S.C. 154(b) by 411 days.

(21) Appl. No.: 10/206,489

(22) Filed: Jul. 26, 2002

(65) Prior Publication Data

US 2004/0034402 A1   Feb. 19, 2004

(51) Int. Cl.⁷ ............................................. A61F 2/06
(52) U.S. Cl. ................................................... 623/1.15
(58) Field of Search ..................... 623/1.15–1.2, 623/1.22, 1.3; 606/194–195

(56) References Cited

U.S. PATENT DOCUMENTS

| 5,913,897 A | 6/1999 | Corso, Jr. et al. ............... 623/1 |
| 6,042,597 A | 3/2000 | Kveen et al. .................. 606/198 |
| 6,129,755 A | 10/2000 | Mathis et al. ............... 623/1.15 |
| 6,190,406 B1 | 2/2001 | Duerig et al. ................. 623/1.2 |
| 6,342,067 B1 | 1/2002 | Mathis et al. ............... 623/1.15 |
| 2002/0116044 A1 * | 8/2002 | Cottone et al. ............... 623/1.2 |

FOREIGN PATENT DOCUMENTS

WO   PCT/US01/16431   5/2001

\* cited by examiner

*Primary Examiner*—(Jackie) Tan-Uyen T. Ho
(74) *Attorney, Agent, or Firm*—Gordon & Jacobson, P.C.

(57) ABSTRACT

A helical stent having a central helically wound portion, and cylindrical ends is provided. A transition zone having struts of different lengths is provided between the helical portion and each cylindrical portion. A junction defining a strut trident is provided between the transition zone and the helical portion. This construction provides a highly flexible stent, permits connecting bridges that are in the same basic orientation, and enables the hoops of the helical, cylindrical, and transitions zones to remain "in phase" such that the stent can easily expand and collapse. According to another aspect of the invention, the kerf between adjacent struts does not go all the way to the end of those struts. The longer struts can have substantially the same flexibility and expansion force as the shorter struts of the transition by making all the kerfs approximately the same length.

22 Claims, 3 Drawing Sheets

HELICAL STENT HAVING FLEXIBLE TRANSITION ZONE

BACKGROUND OF THE INVENTION

1. Field of the Invention

This invention relates broadly to arterial prosthesis. More particularly, this invention relates to vascular stents, and even more particularly to helical stents.

2. State of the Art

Transluminal prostheses are widely used in the medical arts for implantation in blood vessels, biliary ducts, or other similar organs of the living body. These prostheses are commonly known as stents and are used to maintain, open, or dilate tubular structures.

Stents are either balloon expandable or self-expanding. Balloon expandable stents are typically made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly directed force.

Self-expanding stents act like springs and recover to their expanded or implanted configuration after being compressed. As such, the stent is inserted into a blood vessel in a compressed state and then released at a site to deploy into an expanded state. One type of self-expanding stent is composed of a plurality of individually rigid but flexible and elastic thread elements defining a radially self-expanding helix. This type of stent is known in the art as a "braided stent". Placement of such stents in a body vessel can be achieved by a device which comprises an outer catheter for holding the stent at its distal end, and an inner piston which pushes the stent forward once it is in position. However, braided stents have many disadvantages. They typically do not have the necessary radial strength to effectively hold open a diseased vessel. In addition, the plurality of wires or fibers used to make such stents could become dangerous if separated from the body of the stent, where it could pierce through the vessel.

Therefore, recently, self-expanding stents cut from a tube of superelastic metal have been manufactured. These stents are crush recoverable and have relatively high radial strength. Referring to prior art FIG. 1, WPO Patent Application WO 01/89421-A2 (with inventors Cottone and Becker, and referred to herein as "Cottone") describes a self-expanding vascular stent 10 constructed with a helical structure 12 of hoops in the central portion of the stent, a cylindrical hoop 14 of hoops at each end of the stent, and a transition zone 16 joining each cylindrical ends 14 to the central helical portion 12.

The cylindrical-to-helical transition zone 16 is created by splitting a second set of hoops from a cylindrical "turn" so that a loose end results to connect directly to the helical portion. More particularly, Cottone shows a set of transition hoops beginning adjacent to the cylindrical portion, starting at 20 with very short hoops, and the length of the hoops increases circumferentially so that after one circumferential turn around the stent the hoop length at 22 is approximately two times the length of the very short hoop at the beginning of the transition hoops. Cottone shows that the end 24 of the shortest hoop joining the middle of the straight leg 26 (the "strut") of the longest hoop at a junction point 28. From the end of that longest straight leg a new set of hoops (beginning at 30) continues to form the helical central portion 12 of the stent 10. Thus, by joining the beginning 24 of the transition hoops (the "start" of the transition) to the strut 26 of the longest hoop (the "end" of the transition), a "free end" 32 is created that forms the beginning of the helical set of hoops. While this solves the need of creating a free end, it causes a problem because the strut 26 to which the end 24 is joined can not bend sharply at the junction point 28. As a result, there is insufficient flexibility in the short hoop 20 that begins the "start" of the transition. Indeed, the joining of the beginning of the transition section to the middle of the end hoop (the "junction point") creates an overly-rigid portion of the transition zone 16. This rigidity is caused by the inability of the strut 26 of the long hoop 22 to move in the direction of the short attached "start" hoop 20.

The construction shown in Cottone causes the helical hoops 12 to be "out of phase" with the short hoops at the beginning of the transition portion 16. This is because from the junction point 28, the helical hoops begin with a "forward" strut 32, and the transition hoops begin with a "backward" strut 34. As such, connecting bridges 36 are in different orientations, preventing the stent from easy expansion and collapse.

In addition, referring to prior art FIG. 2, the transition zone 16 defined by Cottone is in the form of a generally triangular section in which each successive strut around the circumference from the start of the transition to the end of the transition is longer than the previous strut. If each strut is to contribute equally to the overall radial compressive stiffness and strength of the stent, the struts must be adjusted in width (or other changes made, such as adjustment of the width of the half-loops which connect adjacent struts). That is, a longer strut must be stiffer (by thickening either the width or thickness) in relation to its length so that it will "open" or expand with the same force as a shorter strut. In a triangular transition zone as described by Cottone, each individual strut must be designed such that its width is in approximate proportion to the cube root of the length.

U.S. Pat. No. 6,190,406 to Duerig et al. teaches that the width along the length of a strut is preferably variable and in proportion to the cube root of the distance from point along the strut to the end of the strut. Using the same analysis, it is clear that for a strut of constant width, that width should be in proportion to the cube root of the length of the strut if it is desired to have an even expansion of all the struts of the stent. Duerig does not teach struts of different lengths, but rather teaches how to make tapered struts that minimize the peak strains in a bending situation. Cottone teaches struts of different lengths in the transition zone, but does not address the problems caused by these struts having widely different stiffness.

Moreover, adjusting the width of transition struts to create the proper stiffness for their length causes design compromises because there is not necessarily enough space about the stent to make the width of a long strut at the desired dimension without taking space away from the shorter struts. Doing so would cause the struts to be unequally distributed around the circumference.

SUMMARY OF THE INVENTION

It is therefore an object of the invention to provide a cut tube self-expanding stent which has improved flexibility.

It is another object of the invention to provide a cut tube helical stent which can be easily expanded and collapsed.

It is a further object of the invention to provide a helical stent which has an improved transition zone between a helical portion and an end cylindrical portion.

It is also an object of the invention to provide a stent which has a transition zone of struts of different lengths, wherein the struts of the transition zone have respective stiffness to permit an even expansion of the stent.

It is an additional object of the invention to provide a stent having an even distribution of struts.

In accord with the invention, which will be described in detail below, a helical stent having a central helically wound portion provided with cylindrical end portions is provided. A transition zone having struts of different lengths is provided between the helical portion and each cylindrical end portion.

According to one aspect of the invention, a junction defining a strut trident is provided between the transition zone and the helical portion. This construction reduces or eliminates the overly-rigid section in the transition taught by Cottone in the prior art. In addition, this construction permits connecting bridges that are in the same basic orientation, and the hoops of the helical, cylindrical, and transitions zones remain "in phase" such that the stent can easily expand and collapse.

According to another aspect of the invention, the kerf between adjacent struts does not necessarily have to go all the way to the end of those struts. The kerf can be made shorter, resulting in shorter flexible segments to the strut and a non-flexing "tab" at the end of the struts which is not separated by the kerf. By designing the kerf lengths appropriately, the longer struts can be made less flexible without having to increase their width (or thickness) to accommodate the longer strut length. In fact, in this manner, the longer struts can have substantially the same flexibility and expansion force as the shorter struts of the transition by making all the kerfs approximately the same length.

Additional objects and advantages of the invention will become apparent to those skilled in the art upon reference to the detailed description taken in conjunction with the provided figures.

BRIEF DESCRIPTION OF THE DRAWINGS

Prior art

Prior art

DETAILED DESCRIPTION OF THE PREFERRED EMBODIMENTS

Figure 1:
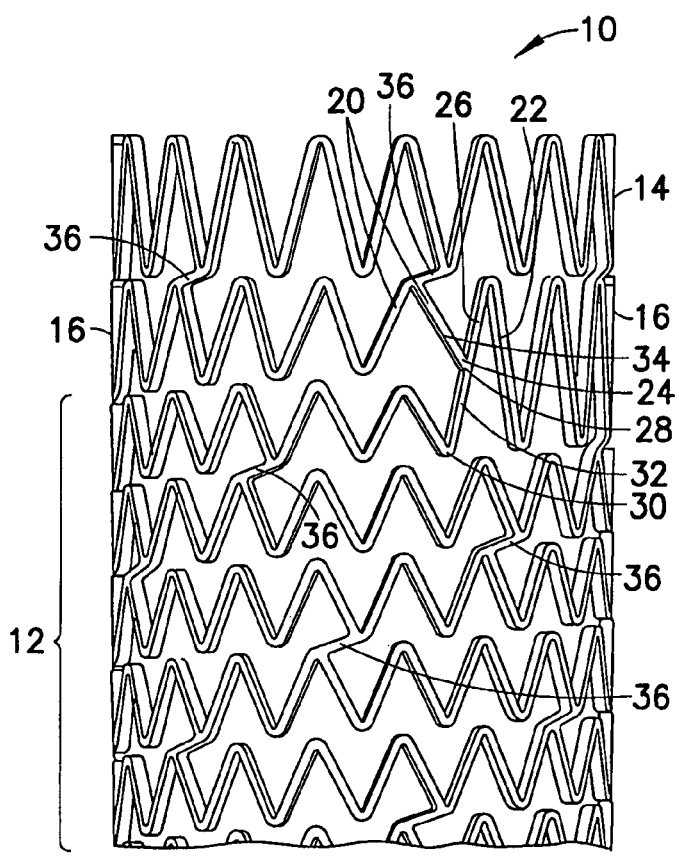
FIG. 1 is a broken side elevation view of a prior art helical stent having a cylindrical end and a transition zone between the helical portion and the cylindrical end and in an expanded state.
Figure 2:
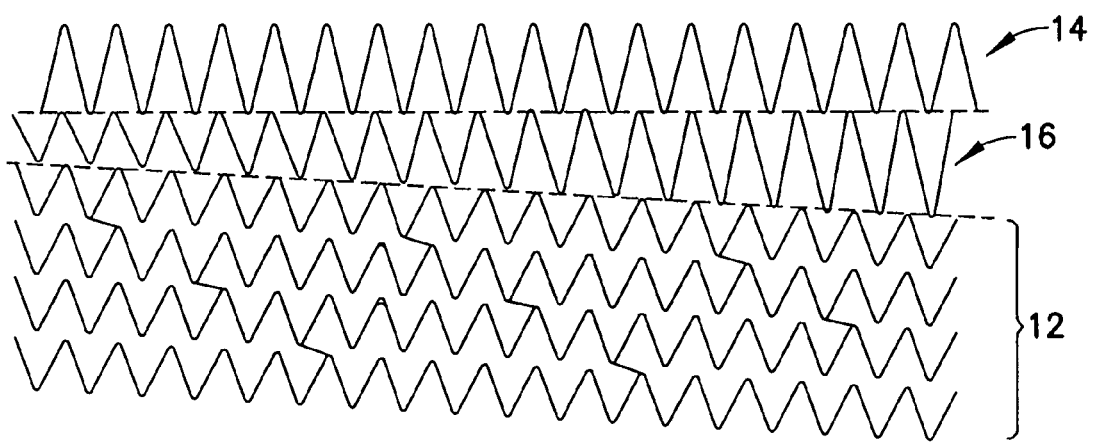
FIG. 2 is a broken flattened view of the prior art helical stent of FIG. 1 in an expanded state, wherein the stent has been cut parallel to its longitudinal axis and laid flat.
Figure 3A:
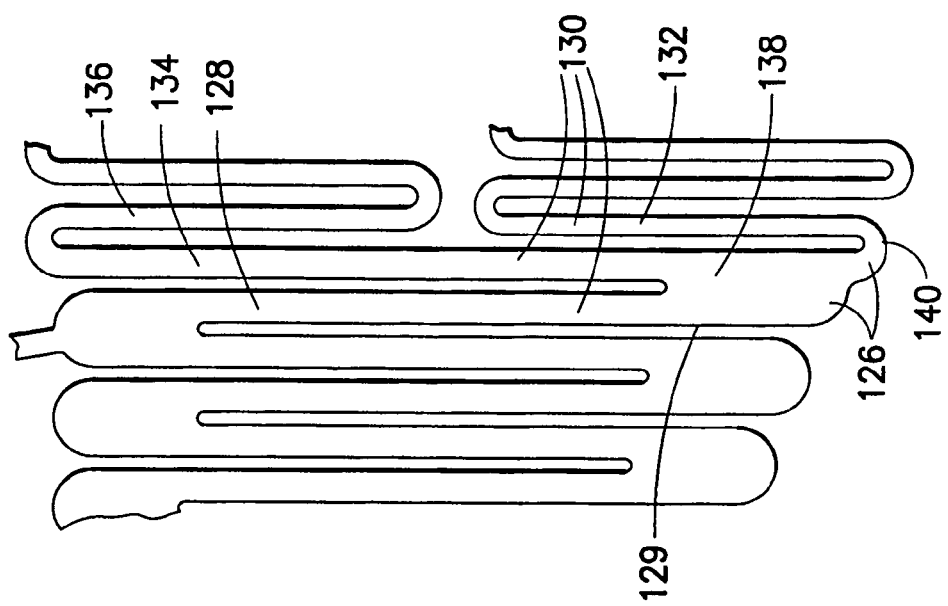
FIG. 3a is an enlarged section of a first embodiment of a three-way connection shown in FIG. 3.
Figure 3:
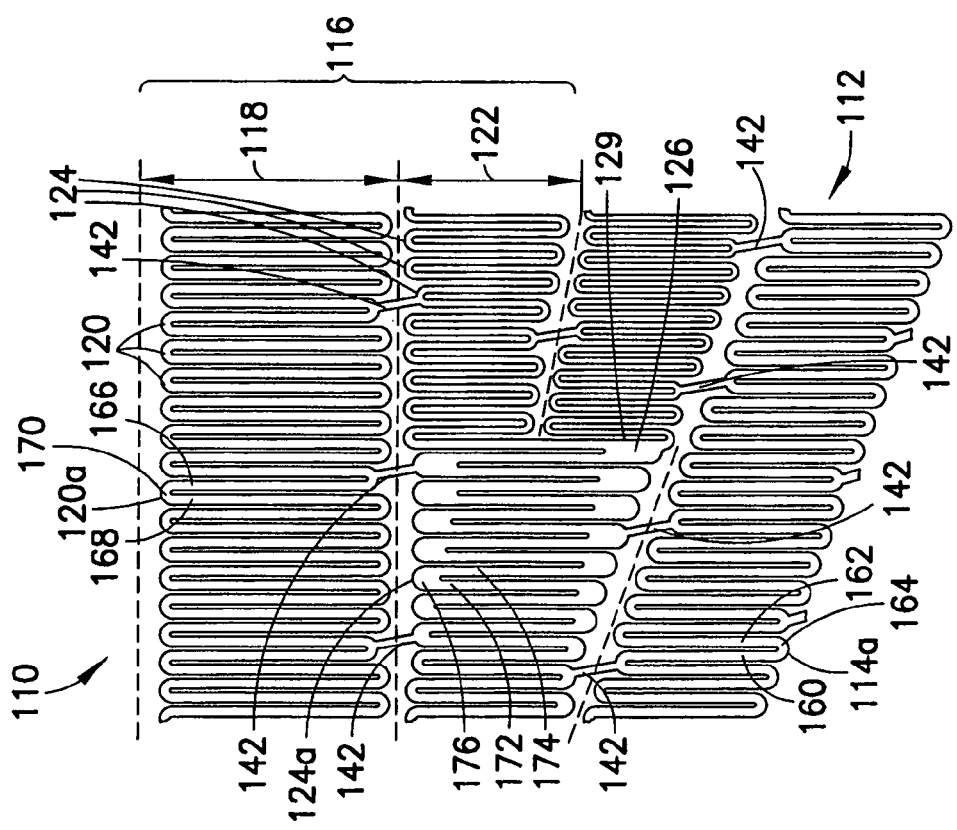
FIG. 3 is a broken flattened view of a first embodiment of a helical stent according to the invention in an unexpanded state, wherein the stent has been cut parallel to its longitudinal axis and laid flat.

Turning now to FIG. 3, a helical stent 110 according to the invention is shown. The stent 110 includes a central helically wound portion 112 (only part of which is shown) defined by hoops 114 and two ends, only one of the ends 116 being shown. Each end 116 preferably includes a cylindrical or crown portion 118 defined by hoops 120 and a transition zone 122 defined by hoops 124, the transition zone 122 being located between the cylindrical portion 118 and the helical portion 112. All hoops are defined by two adjacent struts and a loop-like hinge connecting the struts. For example, in the helical portion, a hoop, e.g. hoop 114a, is comprised of struts 160, 162 and hinge 164, and in the cylindrical portion, a hoop, e.g. hoop 120a, is comprised of struts 166, 168 and hinge 170. In the transition zone, a hoop, e.g. hoop 124a is comprised of struts 172, 174 of different lengths and a connecting hinge 176. The strut length along the helical portion is relatively constant except near the transition zone, where the struts decrease in length, the strut length at the cylindrical portion is relatively constant, and the struts of the transition zone vary in size, generally progressively increasing in length.

When the stent is in a compressed state, the struts of the helical portion, cylindrical portion and transition zone all extend in substantially parallel to the longitudinal axis of the stent. In an expanded state, adjacent struts are moved apart and angled relative to each other.

Referring to FIGS. 3 and 3a, in accord with the invention, a junction 126 is formed where the start of the transition zone 122 joins the end of the transition zone. Junction 126 is located at the end of the longest hoop 129. In the preferred embodiment, the junction 126 forms the base of a three-way division, or trident 130, which is located at the "inner" end of the longest hoop 129 at the end of the transition zone 122 (the strut end which is farthest from the cylindrical portion 118 and nearest the helical portion 112 of the stent). One outside leg of the trident 130 is a strut 128 of the longest hoop 129 of the transition zone 122; the other outside leg 132 is the first strut at the beginning of the helical hoops 114; and, the middle leg 134 is the longest strut 134 which joins to the short leg 136 at the beginning of the transition zone 122. In this design, the flexibility of the hinge (or tab) 138 joining legs 128 and 134 is substantially independent of the hinge 140 joining legs 132 and 134 so that the displacement of these legs is substantially decoupled. This construction reduces or eliminates the overly-rigid section in the transition taught by Cottone in the prior art. In addition, it is noted that all of the connecting bridges 142 which join adjacent turns of the stent are all in the same basic orientation and the hoops remain "in phase" and the stent can easily expand and collapse.

Figure 4:
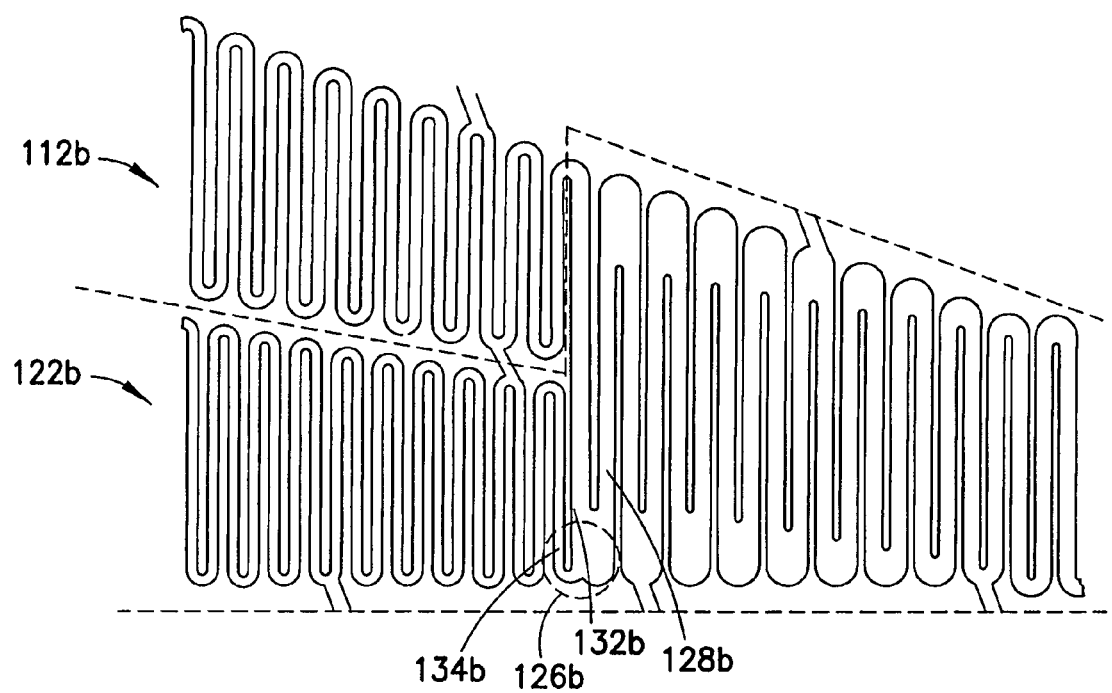
FIG. 4 is a broken flattened view of a second embodiment of a helical stent according to the invention, wherein the stent has been cut parallel to its longitudinal axis and laid flat.

Referring now to FIG. 4, a second embodiment of a junction between the transition zone and the helical portion is shown. According to the second embodiment, the junction 126b defining the "trident" is configured at the "outer" end of the longest hoop 129 (FIG. 3) of the transition zone 122b. In this construction, the long strut 128b at the end of the transition is one outer leg of the trident; the first (short) strut 134b at the beginning of the transition is a second outer leg of the trident; and the longest strut 132b that connects the transition zone 122b to the beginning of the helical portion 112b of the stent is a middle leg of the trident.

From the above, the trident is seen to be comprised of two struts of a common hoop at the end of the transition zone, as well as an adjacent strut which is connected to either the beginning of the transition zone or the helical portion. The junction of the trident includes the hinge of the common hoop, as well as a hinge connecting the adjacent strut to the hinge of the common hoop.

Figure 5:
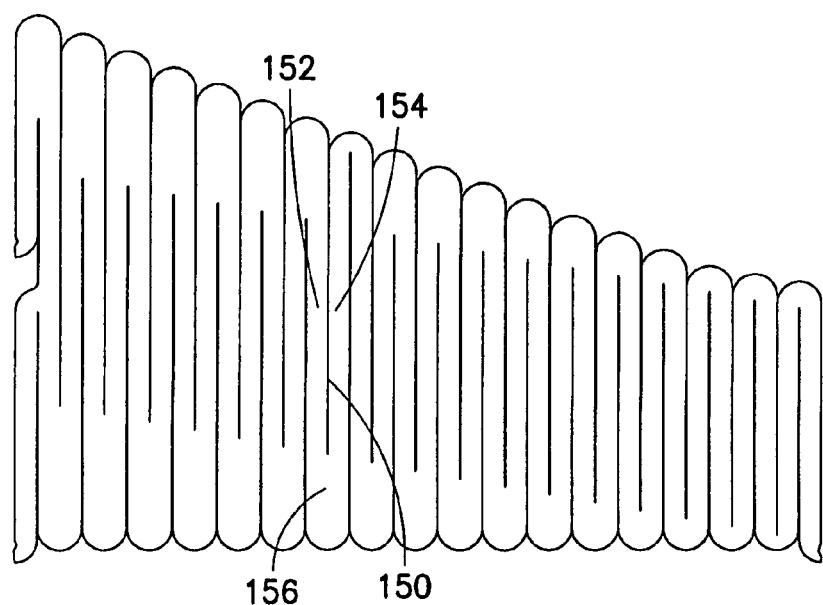
FIG. 5 is a broken flattened view of a transition zone and a helical portion of a stent according to the invention, wherein the stent has been cut parallel to its longitudinal axis and laid flat.

Furthermore, as discussed above, the transition zone 122 has struts 125 of different lengths, and each strut has a width that gives that strut the same opening stiffness as other struts of different lengths. The problem of strut stiffness found in the Cottone prior art is ameliorated by not having the full length of a strut contribute to its flexibility. That is, referring to FIG. 5, the kerf 150 between two adjacent struts 152, 154 does not necessarily have to go all the way to the end of those struts. The kerf 150 can be made shorter, resulting in shorter flexible segments to the strut and a non-flexing "tab" 156 at the end of the struts 152, 154 which is not separated by the kerf 150. Each tab 156 has a length substantially greater than a width of the struts to which it is connected.

By designing the kerf lengths appropriately, the longer struts can be made less flexible without having to increase their width (or thickness) to accommodate the longer strut length. In fact, in this manner, the longer struts can have substantially the same flexibility and expansion force as the shorter struts of the transition by making all the kerfs approximately the same length. As a result, the tabs 156 will vary in size.

There have been described and illustrated herein several embodiments of a stent. While particular embodiments of the invention have been described, it is not intended that the invention be limited thereto, as it is intended that the invention be as broad in scope as the art will allow and that the specification be read likewise. Thus, different aspects of the invention can be used separated or together; e.g., constant kerf length and/or variable tab length can be used in conjunction with stent designs of the prior art to improve those stents and need not be used with the trident junction described herein. It will therefore be appreciated by those skilled in the art that yet other modifications could be made to the provided invention without deviating from its spirit and scope as claimed.

What is claimed is:

1. A stent for insertion into a vessel of a patient, comprising:
   a tubular member having a first smaller diameter for insertion into the vessel, and a second larger diameter for deployment within the vessel,
   said tubular member including a helical central portion, a substantially cylindrical end portion, and a transition zone connecting said central portion and said end portion,
   said helical central portion including a first plurality of hoops substantially a first size, said first plurality of hoops being helically wound,
   said cylindrical end portion including a second plurality of hoops of substantially a second size,
   said transition zone including a plurality of transition hoops having a plurality of different sizes, said hoops of each of said helical central portion, said cylindrical end portion, and said transition zone defined by struts,
   said tubular member having a three-way junction of struts comprising one strut of a last hoop of said transition hoops, one strut of a first hoop of either said transition hoops or said first plurality of hoops, and a middle strut.

2. A stent according to claim 1, wherein:
said transition hoops generally increase in size.

3. A stent according to claim 1, wherein:
said first hoop of said transition hoops has a shortest strut of said transition hoops.

4. A stent according to claim 1, wherein:
said last hoop of said transition hoops has a longest strut of said transition hoops.

5. A stent according to claim 1, wherein:
said middle strut is a longest strut of said transition zone.

6. A stent according to claim 1, wherein:
said middle strut is a strut connecting a strut of a first hoop of said first plurality of hoops to a first or shortest strut of said transition zone.

7. A stent according to claim 1, further comprising:
first connecting bridges connecting said cylindrical end portion to said transition zone,
second connecting bridges connecting said transition zone to said helical portion, and
third connecting bridges connecting longitudinally displaced helically wound hoops of the helical portion,
each of said first, second and third connecting bridges extending in substantially a same orientation.

8. A stent according to claim 1, wherein:
said first plurality of hoops, said second plurality of hoops, and said transition hoops are in phase.

9. A stent according to claim 1, wherein:
each hoop of said transition hoops includes a kerf which separates adjacent struts of said transition hoops, and, for at least one of said transition hoops, said kerf terminates before an end of said hoop thereby forming a tab, said tab having a length substantially greater than a width of said struts of said at least one transition hoop.

10. A stent according to claim 9, wherein:
said kerfs of said transition hoops are substantially a same length.

11. A stent according to claim 1, wherein:
said struts of said helical central portion have a substantially common width.

12. A stent according to claim 1, wherein:
said three-way junction of struts forms a trident.

13. A stent for insertion into a vessel of a patient, comprising:
   a tubular member having a first smaller diameter for insertion into the vessel, and a second larger diameter for deployment within the vessel,
   said tubular member including a helical central portion, a cylindrical end portion, and a transition zone connecting said central portion and said end portion,
   said helical central portion including a first plurality of helically wound hoops,
   said cylindrical end portion including a second plurality of hoops all of substantially a first size,
   said transition zone including transition of hoops of a plurality of different sizes,
   said hoops of each of said helical central portion, said cylindrical end portion, and said transition zone defining struts,
   each transition hoop including a kerf which separates adjacent struts of each said hoop thereof, and, for at least one of said transition hoops, said kerf terminates before an end of said hoop thereby forming a tab, and for at least one of said transition hoops, said struts each have a substantially constant width along said kerf, wherein said tab has a length substantially greater than the substantially constant width of said struts.

14. A stent according to claim 13, wherein:
for a plurality of said transition hoops, said kerfs terminate before ends of said hoops such that tabs are defined at said ends of hoops, said tabs having lengths substantially greater than widths of said struts of said plurality of transition hoops.

15. A stent according to claim 13, wherein:
said kerfs of said transition hoops are substantially a same length.

16. A stent according to claim 13, wherein:
said struts of said helical central portion have a substantially common width.

17. A stent according to claim 13, further comprising:
first connecting bridges connecting said cylindrical end portion to said transition zone,
second connecting bridges connecting said transition zone to said helical portion, and
third connecting bridges connecting longitudinally displaced helically wound hoops of the helical portion,
each of said first, second and third connecting bridges extending in substantially a same orientation.

18. A stent according to claim 13 wherein:
said first plurality of hoops, said second plurality of hoops, and said transition hoops are in phase.

19. A stent for insertion into a vessel of a patient, comprising:
a tubular member having a first smaller diameter for insertion into the vessel, and a second larger diameter for deployment within the vessel,
said tubular member including a helical central portion, a cylindrical end portion, and a transition zone connecting said central portion and said end portion,
said helical central portion including a first plurality of helically wound hoops,
said cylindrical end portion including a second plurality of hoops all of substantially a first size,
said transition zone including a plurality of transition hoops having a plurality of different sizes, said hoops of each of said helical central portion, said cylindrical end portion, and said transition zone defining struts,
each hoop of said third plurality of hoops of said transition zone is defined by a kerf which separates adjacent struts of each said hoop thereof, and, for at least a plurality of said hoops in said transition zone, said kerfs are of a substantially same length.

20. A stent according to claim 19, wherein:
said struts of said helical portion have a substantially common width.

21. A stent according to claim 19, further comprising:
first connecting bridges connecting said cylindrical end portion to said transition zone,
second connecting bridges connecting said transition zone to said helical portion, and
third connecting bridges connecting longitudinally displaced helically wound hoops of the helical portion,
each of said first, second and third connecting bridges extending in substantially a same orientation.

22. A stent according to claim 19, wherein:
said first plurality of hoops, said second plurality of hoops, and said transition hoops are in phase.

* * * * *